United States Patent [19]

Dorsey, III

[11] Patent Number: 5,188,591
[45] Date of Patent: Feb. 23, 1993

[54] IRRIGATION CONTROL VALVE FOR ENDOSCOPIC INSTRUMENT

[76] Inventor: James H. Dorsey, III, 901 E. Sample Rd., Suite C, Pompano Beach, Fla. 33064

[21] Appl. No.: 470,771

[22] Filed: Jan. 26, 1990

[51] Int. Cl.$^5$ ............... A61M 1/00; F16K 11/00
[52] U.S. Cl. ...................... 604/33; 604/35; 604/118; 604/119; 604/249; 137/596.2; 251/325
[58] Field of Search ............... 604/27-35, 604/118, 119, 246-249, 121, 173, 184, 243; 137/596, 596.2; 251/325; 91/454

[56] References Cited

U.S. PATENT DOCUMENTS

| | | | |
|---|---|---|---|
| 1,056,753 | 4/1913 | O'Brien et al. | 251/325 |
| 2,669,233 | 7/1951 | Friend | 604/33 |
| 2,940,465 | 6/1960 | Frantz | 137/596 |
| 3,678,959 | 7/1972 | Liposky | 251/325 |
| 4,457,257 | 5/1984 | Atchley | 251/325 |
| 4,548,197 | 10/1985 | Kinoshita | 604/27 |
| 4,552,130 | 11/1985 | Kinoshita | 604/27 |
| 4,925,450 | 5/1990 | Imonti et al. | 604/248 |
| 4,964,846 | 10/1990 | Robicsek | 604/35 |

*Primary Examiner*—C. Fred Rosenbaum
*Assistant Examiner*—Mark Bockelman
*Attorney, Agent, or Firm*—Malin, Haley, Dimaggio & Crosby

[57] ABSTRACT

An improved irrigation control valve for endoscopic instruments is herein described wherein the valve body is bilaterally symmetrical and includes a housing, a plurality of valve chambers, pistons for reciprocal movement within each of said chambers, an inlet port for connection to a source of an irrigation fluid and a vacuum port for connection to a source of vacuum and symmetrical opposed fittings for mounting a probe in either one of two positions to accommodate both the right handed and left handed clinician. The design of both the pistons and valve body are unique, compatible with injection molding fabrication techniques and further provide for replacement and/or into change of the probe. Such interchange and/or replacement of the probe can be accomplished without clamping off of either the source of irrigation fluid or the source of suction because of the proximal location of the probe connection to the valve body relative to both the irrigation and suction valves. The valve body can be used in conjunction with a variety of probes and in various endoscopic procedures; one of the preferred applications of this invention being in the hydrodissection of gynecological tissue.

4 Claims, 2 Drawing Sheets

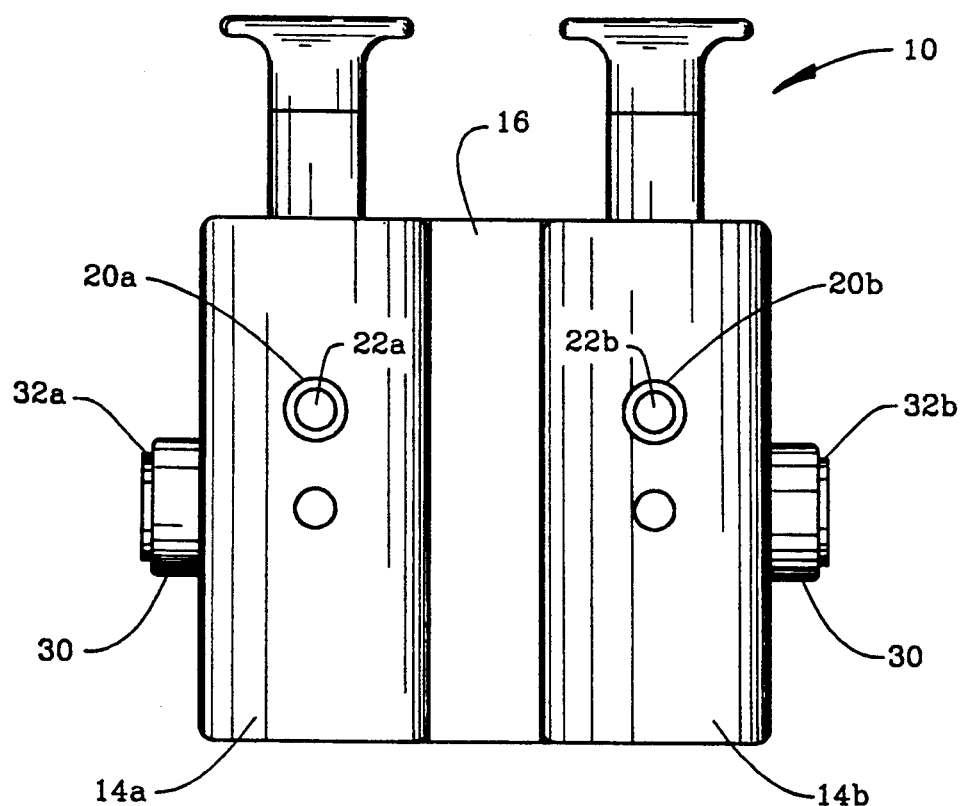
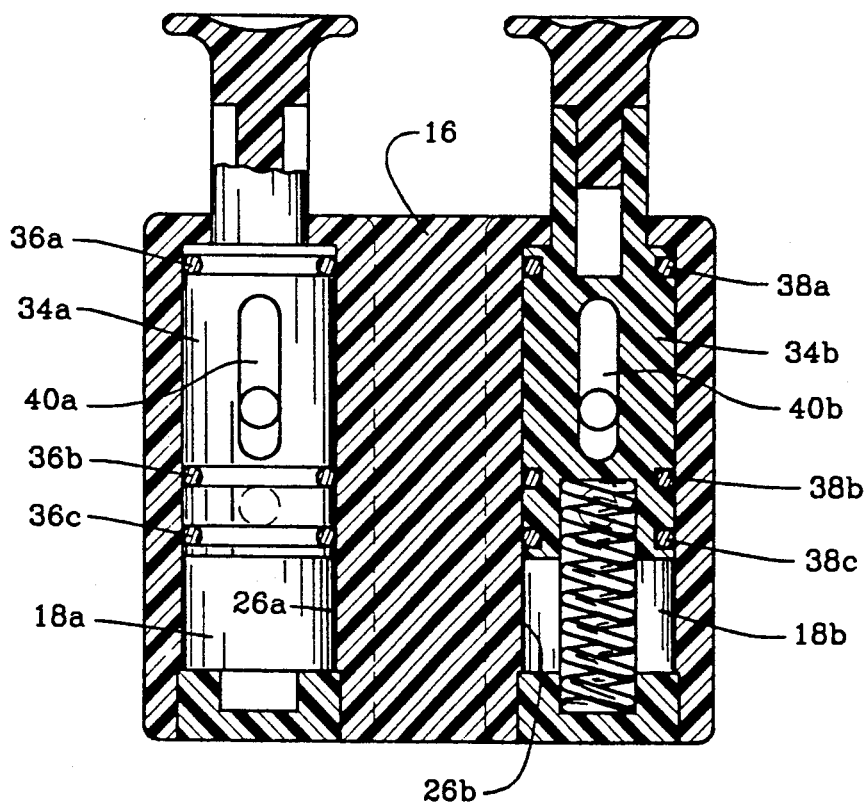

IRRIGATION CONTROL VALVE FOR ENDOSCOPIC INSTRUMENT

BACKGROUND OF THE INVENTION

1. Field of the Invention

This invention is directed to a device, a system and to a method. More specifically, this invention relates to an improved irrigation control valve for use in conjunction with endoscopic instrumentation, an endoscopic instrument system incorporating the improved irrigation control valve and to a method for hydrodissection of tissue.

The design of the improved irrigation control valve lends itself to injection molding techniques and is also unique in its ready adaptation to both right and left handed operation due to the symmetry of the valve body and the adaptation of the valve body to interchangeable probe tips. Accordingly, the probe can be mounted in either one of two positions to accommodate the clinician's preference.

2. Description of the Prior Art

The field of endoscopy and the problems associated therewith are well-known and need not be repeated herein. Whether the endoscope is rigid or flexible, equipped with a telescope and light source or fluoroscopic means required for the guidance and manipulation within the operative field, one problem is generally common to both types of system—the difficulties encountered in the infusion and suction of fluid for clearance of the operative field. The following patents are representative of endoscopic instruments available to the clinician and the various applications thereof: U.S. Pat. Nos. 4,191,191; 3,967,625; 4,824,434; 4,735,194; 4,795,424; 4,504,493; 4,493,320; 4,423,727; 4,217,819; and 4,795,424.

The controlled irrigation of an operative field typically involves regulation of the flow rate of the irrigant fluid through a probe tip by means of conventional stop cock valves or a mechanical equivalent, see for example U.S. Pat. Nos. 4,795,424 (to Burner); see also 4,795,424; 4,493,320; 4,423,727; and 4,217,891.

In the state of the art endoscopic devices presently in use, irrigation has typically been subordinated in both sophistication and importance to the surgical implements which are used with these devices, with the possible exception of the field of hydrodissection. In hydrodissection, a pressurized irrigation fluid is directed through a probe onto the operative field to effect removal of a target tissue. Alternating activation of the irrigation and suction valves effects removal of the infused fluid, fluid endogenous to the operative field and any tissue that has been hydraulically displaced. In the field of hydrodissection, the endoscopic instrument generally consists of a valve body having means for connection to both a souce of irrigation fluid and a source of suction. In this type of instrument, a probe is generally permanently affixed to the valve body which provides the means for direction of the fluid onto the operative field. Hydrodissection instruments are currently commericially available.

As is evident from review of the commercially available endoscopic devices irrigation has and remains at a relatively primitive level of sophistication. This is also the case in the endoscopic instruments specifically designed for hydrodissection. All of these devices are generally limited in that the design is biased in favor of either a right or left handed individual; the probe tip is generally permanently affixed to the valve body; where the probe tip can be removed and/or changed, such manipulation requires separate closure of both irrigant and suction lines; and, upon completion of the operative procedure, both the valve along with the probe tip are typically discarded.

OBJECTS OF THE INVENTION

It is the object of this invention to remedy the above as well as related deficiencies in the prior art.

More specifically, it is the principal object of this invention to provide an irrigation control valve having a design compatible with plastic injection molding techniques.

It is another object of this invention to provide an endoscopic instrument system equipped with an irrigation control valve having a symmetrical valve body and interchangeable probe tips.

It is a further object of this invention to provide an endoscopic instrument system incorporating a symmetrical irrigation control valve which can be readily configured for right or left handed operation, depending upon the placement and/or connection of the probe tip.

It is yet a further object of this invention to provide an endoscopic instrument system incorporating a symmetrical irrigation control valve having interchangeable probes and a method for the use of such endoscopic system in hydrodissection procedures.

SUMMARY OF THE INVENTION

The above and related objects are achieved by providing an improved irrigation control valve which is bilaterally symmetrical; that is symmetrical along the plain coincident with the attachement probe to the valve body and symmetrical along the plain between the two valves. As noted hereinabove, and once again emphasized, the unique design of this irrigation control valve lends itself to plastic injection molding techniques and, because of its unique symmetrical design, permits the attachment of the probe to the valve body at either one of two positions, depending upon clinician preferences. The valve body is a relatively simple structure having a plurality of cylinders, each of which is provided with a corresponding piston. Each of these cylinders is further provided with an orifice. In the case of the fluid control valve, the orifice of the cylinder is simply a continuation of the conduit formed by the fitting which is adapted to connection to the source of irrigation fluid. Similarly, the inlet orifice for the suction control valve is simply a continuation of the conduit of the fitting adapted for connection to the source of suction. The cylinder is provided with a second orifice which provides for communication between the cylinder and a second (common) conduit. This common conduit is disposed at right angles to the longitudinal axis of the cylinder. The common conduit is adapted at both ends with a fitting for connection to a probe. The vacuum control cylinder is similarly provided with an orifice which provides for communication between the interior of the cylinder to a source of vacuum and a second orifice, which provides communication between the interior chamber of the cylinder and the common conduit. Both in the cylinder for the fluid control valve and in the cylinder for the vacuum control valve, the inlet orifice and the orifice to the common conduit are offset relative to one and other. The irrigation control valve is further provided with a reciprocating piston for each cylinder. The construction of the piston for each cylinder is substantially the same in that the barrel of the cylinder is provided with an oval shaped opening which extends between a first barrel seal to a second barrel seal. Upon reciprocation of the piston within the cylinder, the valve is opened by effecting communication between the inlet orifice and the orifice to the common conduit through the oval opening in the barrel of the piston. The degree to which the piston is reciprocated within the cylinder modulates the flow between the inlet orifice and the orifice to the common conduit, be that flow of irrigation fluid or degree of vacuum. A third seal is provided at the base of the cylinder to prevent fluid from accumulating between the end of the piston and the portion of the valve body chamber in which the spring is contained.

The design and construction of the irrigation control valve, most notably the positioning (offset) of the orifice from the inlet port relative to the orifice to the common conduit and the shape of the opening within the barrel of the piston provide this valve with the unique capability of simplicity in manufacture and enhancement in control of flow and/or suction between the common conduit and the port which connects the respective chambers of the valve to the source of irrigation fluid and to the source of suction.

BRIEF DESCRIPTION OF THE DRAWINGS

FIG. 1 is a plan view of a symmetrically irrigation control valve of this invention.

FIG. 2 is a sectional view, along the horizontal plain, of the irrigation control valve of FIG. 1.

DESCRIPTION OF THE INVENTION INCLUDING PREFERRED EMBODIMENTS

Figure 3:
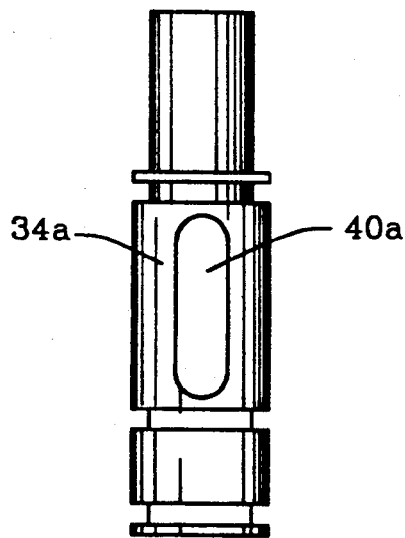
FIG. 3 is a plan view of a piston of the irrigation control valve of FIG. 1.

The preferred embodiments of this invention are illustrated in reference to the foregoing enumerated figures. For ease of discussion and simplification of description, a common reference numeral is assigned to a particular component feature of the irrigation control valve and such common reference numeral used within each of the figures.

In the illustration of this invention shown in FIG. 1, the irrigation valve (10) comprises a valve housing or (12) body having two valve chambers (14a, 14b), one valve chamber adapted for communication between a common conduit (16) of the control valve and a source of irrigation fluid (not shown) and a second valve chamber for communication between a source of suction (not shown) and a common conduit (16) of a the control valve body. In each instances, the common conduit of the control valve is provided with a probe (not shown). This probe can be connected to either the right hand or left hand fitting located on the side of the control valve. The positioning of the probe relative to the body of the control valve will be based upon clinician preference—whether the clinician is right handed or left handed. In either instance the control valve will operate essentially the same. It is also important to note that in the embodiment of this illustrated herein either chamber (18a, 18b) of the control valve can be connected to either a source of vacuum or a source of irrigation fluid in that both chambers, and, thus, in the preferred embodiments of this invention, are essentially the same. In each instance the irrigation control valve of this invention comprises a valve housing or body within which are formed two cylindrical valve chamber. The housing of the control valve is further equipped with a pair of fittings (20a, 20b) for each chamber which defines a conduit (22a, 22b). The fitting can be connected to a source of vacuum or a source of irrigation fluid. These conduits (22a, 22b) provide communication between the source of vacuum and/or irrigation fluid and the interior of the valve chamber which is formed within the body of the control valve. The valve chamber is essentially uniform in diameter and of a defined length.

Figure 5:
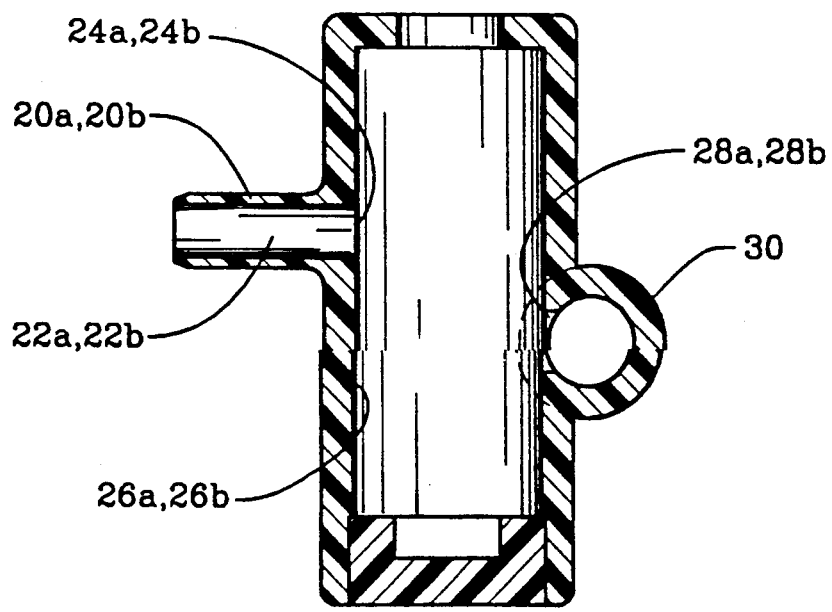
FIG. 5 is a sectional view of the irrigation control valve of FIG. 1 AA.

As more completely illustrated in FIGS. 2 and 5, the valve body defines two interior cylindrical chamber (18a, 18b), each of which is essentially the same in both dimension and in its contemplated operation. Each such chamber is of a defined length. The fitting or inlet port on the valve body defines a conduit which terminates as an inlet orifice (24a, 24b) in the chamber wall (26a, 26b). The chamber wall is provided with yet a second orifice (28a, 28b), offset from the inlet orifice. This second orifice provides for communication between the interior of the chamber and a conduit (30) which is at right angles to the orientation of the chamber. This conduit is provided on either end with a fitting (32a, 32b) adapted to connect to a probe (not shown).

Figure 4:
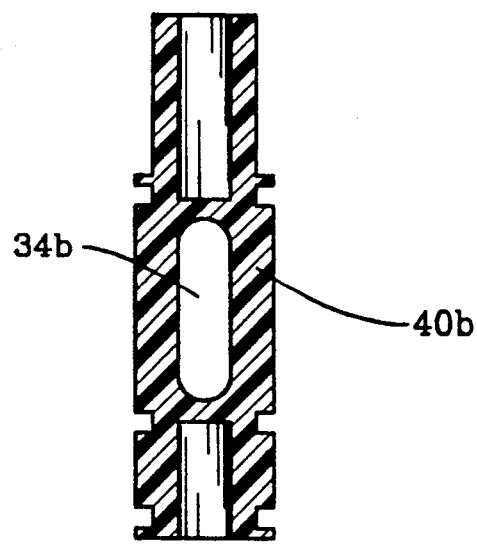
FIG. 4 is a sectional view, along the horizontal plain of the piston of FIG. 3.

Each of the valve chambers within the valve body is further provided with a piston (34a, 34b). As more fully illustrated in FIGS. 2, 3 and 4, these pistons are designed for reciprocating movement within the cylinder. In order to provide for watertight and airtight operation, these pistons are each equipped with a series of seals (36a-c, 38a-c). Each piston is further provided with an oval opening (40a, 40b) approximately equivalent in width to the orifices in the chamber wall. The length of the piston is such as to allow reciprocating movement within the cylindrical chamber and accommodation of spring bias means (not shown) within the cylinder chamber between the base of the piston and the bottom of the cylindrical chamber. The spring bias means is intended to maintain the valve in the closed portion.

The seals which are located both fore (36a, 38a) and aft (36b, 38b) to the oval opening (40a, 40b) in the piston prevent fluid from inadvertently flowing from the source of irrigation fluid to the common conduit. As the cylinder is depressed (in the direction indicated by the arrow), and the oval opening in the piston aligned to permit communication between the inlet orifice and the orifice to the common conduit, fluid will begin to flow therebetween. The seal at the base of the piston ensures against fluid being trapped between the base of the piston and the base of the valve chamber which, if not vented, could prevent depression of the piston within the chamber.

FIG. 5 illustrates the relative positioning of the two orifices within each cylinder wall and the contemplated direction of flow of fluid upon reciprocal movement of the piston to allow for such flow.

In operation of this valve, a conduit is connected to each of the fittings on the valve body. The conduit can be connected to either a source of irrigation fluid or to a source of vacuum. For the purpose of simplification of description, it is assumed the conduit is connected to a source of irrigation fluid. Upon depression of the piston, the oval shaped opening in the piston barrel effects communication between the inlet orifice and the piston wall and the orifice of the common conduit thereby allowing for flow of fluid therebetween. The further the piston is depressed within the valve chamber, the greater the flow of fluid therethrough.

The improved irrigation control valve illustrated and described herein above is but representative of the preferred embodiments of this invention and not intended as delineating the scope thereof, which is set forth in the following claims.

What is claimed is:

1. An improved irrigation control valve assembly comprising a bilaterally symmetrical housing defining a plurality of valve chambers, each such valve chamber comprising an elongate cylinder, a piston and means for reciprocating movement of said piston within said valve chamber, each said valve chamber being further provided with an inlet orifice connected to a source of vacuum or irrigation fluid and a second orifice, axially offset from the inlet orifice, connected to a common conduit, the piston for each chamber of the valve assembly being of a defined length relative to the length of such valve cylinder to allow for reciprocating movement of each said piston within said cylinder, each said piston being further provided with an elongate aperature, the size and shape of which being determined by the relative distance between the orifices within the valve cylinder wall and controlled flow of fluid, upon reciprocating movement of said piston, within said cylinder thereby allowing for communication between the orifices in said cylinder wall through the elongate aperature in said piston; and a common conduit formed at right angles relative to the cylinders of said valve body and communicating with each cylinder in said valve body through the second orifice in the cylinder wall, the common conduit being provided with a fitting adapted for connection to a probe, said valve being further characterized as having at least one (1) pair of chambers within a housing that is symmetrical about a plane containing a wall that separates the valve chambers, said housing being adapted for attachment of a probe to the valve housing at either one of two positions to accommodate clinician preference.

2. The value of claim 1, wherein the elongate aperature is of an essentially oval shape.

3. The value of claim 1 wherein the housing is provided with means for connection of interchangeable probes.

4. An improved irrigation control valve assembly comprising a bilaterally symmetrical housing defining a plurality of valve chambers, each such valve chamber comprising an elongate cylinder, a piston and means for reciprocating movement of said piston within said valve chamber, each such valve chamber being further provided with an inlet orifice connected to a source of vacuum or irrigation fluid and a second orifice, axially offset from the inlet orifice, connected to a common conduit, the piston for each valve chamber of the assembly being of a defined length relative to the length of such valve cylinder to allow for reciprocating movement of each said piston within said cylinder, each said piston being further provided with an elongate aperture, the size and shape of which being determined by the relative distance between the orifices within the valve cylinder wall and affecting the controlled flow of fluid upon reciprocating movement of said piston within said cylinder, allowing for the fluid communication between the orifices in said cylinder wall through the elongate aperture in said piston and the linear modulation of the rate of flow of fluid; and a common conduit formed at right angles relative to the cylinders of said valve body and communicating with each cylinder in said valve body through the second orifice in the cylinder wall, the common conduit being provided with a fitting adapted for connection to a probe, said piston being further characterized as having a plurality of seals, one seal being positioned on said piston above the aperture to preclude fluid flow into the upper portion of the cylinder, a second seal positioned below the aperture to prevent the fluid communication between the inlet and outlet orifice of the cylinder prior to depression of the piston within the chamber and third seal positioned below said second seal to prevent fluid flow from the chamber upon depression of the cylinder upon the establishment of fluid communication between the inlet and outlet orifices of said chamber.

* * * * *